United States Patent [19]
Gudehus

[11] Patent Number: 6,060,720
[45] Date of Patent: May 9, 2000

[54] METHOD AND APPARATUS FOR DETERMINING AND ENCODING LINEAR POSITION BY MEANS OF LENTICULAR SCREENS

[76] Inventor: Donald Gudehus, 1140-H Court Dr., Duluth, Ga. 30096

[21] Appl. No.: 09/160,508

[22] Filed: Sep. 24, 1998

[51] Int. Cl.$^7$ ..................................................... G01N 21/86
[52] U.S. Cl. ...................................... 250/559.29; 347/230
[58] Field of Search ........................... 250/559.29, 559.3; 359/621, 623; 347/230

[56] References Cited

U.S. PATENT DOCUMENTS

| | | | |
|---|---|---|---|
| 5,162,897 | 11/1992 | Jitsukata et al. ........................... | 358/60 |
| 5,812,152 | 9/1998 | Torigoe et al. .............................. | 347/2 |
| 5,818,495 | 10/1998 | Taylor .................................... | 347/226 |
| 5,838,360 | 11/1998 | Harrold et al. ........................... | 347/41 |
| 5,850,580 | 12/1998 | Taguchi et al. .......................... | 359/463 |

*Primary Examiner*—Stephone B. Allen
*Attorney, Agent, or Firm*—Deveau & Marquis; Harold L. Marquis

[57] ABSTRACT

A method of determining linear position by means of lenticular screens in a direction perpendicular to the axes of the lenticules and in the planes of the screens is disclosed comprising the steps of:
  a) directing a collimated beam of radiation perpendicularly into a first sheet of lenticular material;
  b) allowing the beam transmitted by the first sheet to enter a second sheet of similar pitch, oriented parallel to the first sheet, and with the axes of the lenticules parallel to the axes of the first sheet, and spaced so as to recollimate the radiation beam upon exit from the second sheet;
  c) placing a radiation detector array situated to receive the collimated beam exiting from the second lenticular sheet and subtending the field-of-view of the lenticules;
  d) sensing the position of the collimated beam within the field-of-view of the lenticules, and keeping account of the number of transits and fractions thereof of the beam across the center of the field-of-view of the lenticules with the detector array, due to a displacement of the lenticular sheets relative to each other in a direction perpendicular to the axes of the lenticules and in a plane parallel to themselves. Also disclosed is an apparatus for measuring linear displacement, comprising a device for producing a collimated beam of radiation; a reference lenticular sheet; a movable lenticular sheet; and a detector array. Means for encoding the linear displacement is also disclosed.

29 Claims, 5 Drawing Sheets

METHOD AND APPARATUS FOR DETERMINING AND ENCODING LINEAR POSITION BY MEANS OF LENTICULAR SCREENS

FIELD OF THE INVENTION

This invention relates to the field of encoding position along a straight-line path and more specifically to encoding position by means of lenticular screens in a direction perpendicular to the axes of the lenticules, and in the planes of the screens.

BACKGROUND OF THE INVENTION

There are several methods of encoding linear position. In one method, a cable attached to a movable platform is wound around a shaft, which is attached to an encoder of rotary motion. In another, a movable platform is attached to a nut threaded with a lead screw which is attached to a rotary encoder. A variation of this method is to move the platform by a stepper motor and keep count of the steps. Coarser encoding can be accomplished by electrical switches located at known positions which are opened and closed in turn by contact with a projection extending from a movable platform. Similarly, a beam of light, infrared, or other radiation can trigger radiation sensors in turn as the platform moves along a linear path. Although the combinations of lead screw and rotary encoder, or lead screw and stepper motor yield high accuracy, resolution, and repeatability, these methods are costly. Conversely, a series of switches or radiation detectors is economical but does not give very high positional resolution.

Sheets of optically transparent lenticular material are sometimes used for producing three-dimensional depth visualization effects and minor animation effects. In order to achieve these effects, it is necessary that the position on the lenticular material be precisely known in order to provide the depth visualization and animation effects. It is extremely complicated and subject to a high risk of error to manually align the lenticular print material for printing.

PRIOR ART

U.S. Pat. No. 5,424,553 (Morton) discloses several methods for aligning lenticular materials for printing. This alignment is essential prior to the lenticular material passing through a printing press for printing a 3D image on the lenticular material. One of his methods is to direct a light beam so that one of the lenticules focuses the light at the printing surface of the lenticular material. A light sensitive array can be used to determine the location so that the lenticular material can be adjusted to the proper location for printing. A computer can be used to determine the position of the sensor in the array which receives the maximum amount of light. Morton discloses another technique for the alignment of the lenticular material using a second piece of lenticular material of a slightly different pitch. The lenticular material to be aligned is illuminated with the other lenticular material with their planar surfaces being adjacent. This results in forming a Moiré pattern with the lenticular material being aligned at the position where the local intensity is at its maximum. As shown in FIG. 3 of Morton, the curved surfaces of these sheets of lenticular material face in opposite directions.

U.S. Pat. No. 5,689,340 (Young) discloses an apparatus and method for aligning lenticular material by determining the location of an encoded portion adjacent to the lenticules. A light source illuminates the encoded portion and a sensor determines its precise location for subsequent printing.

U.S. Pat. No. 5,699,190 (Young et al.) discloses lenticular print material having an encoded portion for the alignment and registration of the print material. A portion of the lenticular material adjoining the main portion is encoded to provide the alignment and registration of the main portion. This alignment is achieved by machining an encoded lenticular pattern into the portion that is used for alignment of the main portion.

SUMMARY OF THE INVENTION

The present invention provides a method and apparatus for determining and encoding linear position by means of positional measurements of a collimated beam of radiation passing through two parallel sheets of lenticular material of similar pitch. Linear position can be taken to be the displacement in units of lenticules and fractions thereof of one of the sheets relative to the other from some starting position, in a direction parallel to the sheets and perpendicular to the longitudinal axes of the lenticules. The positional measurements can be made with a multi-element radiation sensor large enough to subtend the field-of-view of the lenticules and located so as to intercept the collimated beam of radiation exiting from the last lenticular sheet. The source of radiation, detector of radiation, and one of the lenticular sheets are held fixed relative to each other, and the other sheet is allowed to move. The fixed sheet is known as the reference sheet and need only be somewhat larger than the diameter of the radiation beam. The length of the movable sheet will determine the span of distance that can be measured by this method. The perpendicular separation of the sheets is held constant and at a distance so that the exiting beam of radiation is recollimated after passing through both sheets. Either the convex or plane surface of each sheet may face the incident radiation beam, with the separation of the sheets depending on the actual configuration. The sensor array is used to determine where within the field-of-view the collimated beam is located, and if the beam has split, where the two beams are located. An accounting of the number of times, and fraction thereof, that the beam has transited the central plane in each direction can be accomplished with a microcontroller which accepts and interprets the output of the sensor array. Each transit corresponds to a linear displacement of one lenticule width, with the displacement resolution depending on the number of detector elements within the field-of-view provided that the collimated beam is not greatly oversampled. The microcontroller can also send this linear position to a display device. This position is encoded which can be in the memory of the microcontroller or by marking the lenticular screen, or otherwise. Because an apparatus based on this invention allows the position of any point on the movable lenticular material relative to some reference point to be determined, one can use such an apparatus to measure distance traversed by a movable table from some starting position, to align an external tool or print head to the lenticular material, or conversely to align the lenticular material to a tool or print head.

It is an objective of the present invention to provide a method and apparatus for accurately encoding linear position with high signal-to-noise ratio (e.g., recollimated radiation to stray radiation ratio).

It is an objective of the present invention to provide a method whereby an inexpensive and compact apparatus can be constructed for encoding linear position.

It is yet another objective of the present invention to provide a method and apparatus for accurately aligning lenticular material to some predetermined position.

It is yet another objective of the present invention to provide a method and apparatus for accurately aligning an external object such as an engraving tool or print head to a predetermined position on lenticular material.

It is still another objective of the present invention to provide a method and apparatus for accurately encoding rotational position wherein one end of the lenticular linear encoder is attached to a cable wound around a shaft.

DETAILED DESCRIPTION OF THE INVENTION

Figure 1:
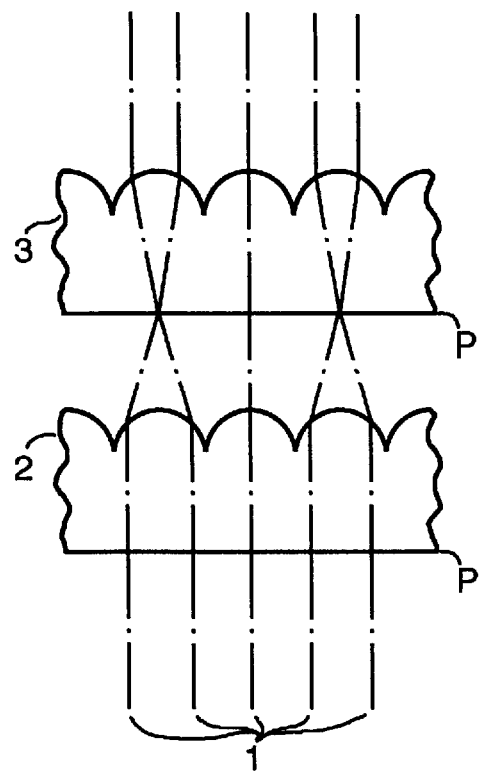
FIG. 1 illustrate the recollimation of a beam of radiation when both lenticular sheets present their plane ides to the incoming radiation.

When a collimated beam of radiation passes through a lenticular sheet, the beam will ultimately diverge. If a small lens of diameter equal to the width of a lenticule is placed on the optical axis of a single lenticule, a position can be found at which the rays of the beam passing through that lenticule will be recollimated and become available for sensing. However if the beam illuminates more than one lenticule on the sheet, those rays passing through the extra lenticules will not be collimated and will act to reduce the signal-to-noise ratio. If on the other hand only a single lenticule is illuminated by the beam in order to reduce the background, then only a small amount of radiation is available to work with, and furthermore, the lens is restricted to locations within the field-of-view of that lenticule. A much more favorable configuration arises when two parallel lenticular sheets of similar pitch are placed with their longitudinal axes parallel and with a spacing such as to allow recollimation of the incident beam. This is illustrated in FIG. 1, where rays 1 comprising part of a perpendicularly incident collimated beam of radiation are focused by a plurality of lenticules contained on lenticular sheet 2 onto the principal focal plane of sheet 2. Because the plane surface P of lenticular sheet 3 is located approximately in the principal focal planes of both sheets, the rays passing through and exiting the plurality of lenticules on sheet 3 are recollimated. It will be understood that the signal-to-noise ratio is high in this configuration because many lenticules are illuminated and because all the rays are recollimated.

Figure 2:
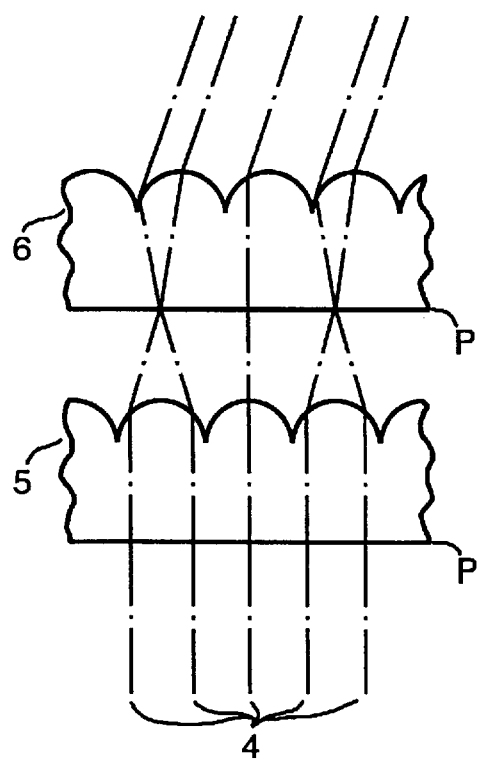
FIG. 2 illustrates the recollimation and deflection of a beam of radiation when both lenticular sheets present their plane sides to the incoming radiation and the relative lateral offset between sheets is about one-quarter lenticule or 90 degrees of phase.

FIG. 2 illustrates the deflection and recollimation of the beam when the lenticular screens are displaced laterally relative to each other by about one-quarter of the width of a lenticule or 90 degrees of phase. Rays 4, which comprise part of a perpendicularly incident collimated beam of radiation are focused by a plurality of lenticules contained on lenticular sheet 5. Lenticular sheet 6, located with its plane surface P in the focal plane of the rays passing through sheet 5, recollimates the rays but deflects them in the direction of its displacement relative to sheet 5 by about one-quarter the field-of-view. It will be understood that the angular deflection of the rays varies continuously from zero to one-quarter the field-of-view as the lateral displacement is continuously varied from zero to 90 degrees of phase.

Figure 3:
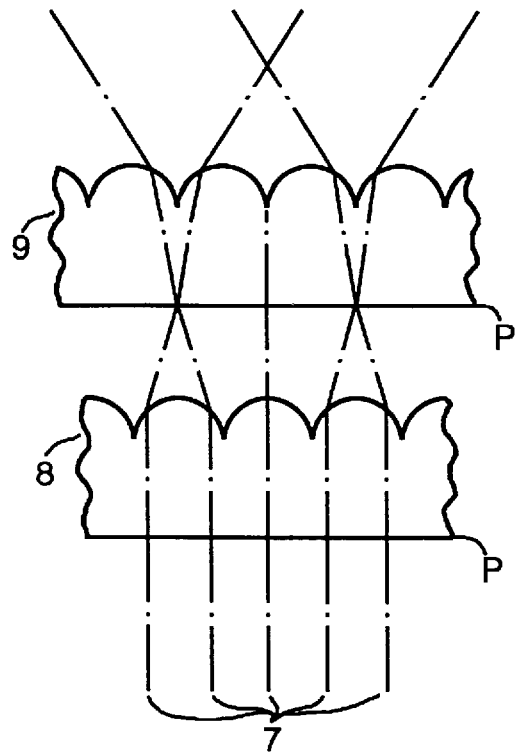
FIG. 3 illustrates the recollimation, deflection, and splitting of a beam of radiation when both lenticular sheets present their plane sides to the incoming radiation and the relative lateral offset between sheets is about one-half lenticule or 180 degrees of phase.

FIG. 3 illustrates the deflection and recollimation of the beam when the lenticular screens are displaced laterally relative to each other by about one-half of the width of a lenticule or 180 degrees of phase. It will be noticed in FIG. 3 that rays 7 passing through sheet 8 are focused onto the focal plane at plane P of sheet 9 as in the case of FIGS. 1 and 2. In other words, the distance between the sheets in FIGS. 1–3 is the same. Rays 7, which comprise part of a perpendicularly incident collimated beam of radiation are focused by a plurality of lenticules contained on lenticular sheet 8. Lenticular sheet 9 located with its plane surface P in the focal plane of the rays, recollimates the rays but splits them, deflecting about one-half of them in the direction of its displacement relative to sheet 8, and about one-half of them in the opposite direction, each by about one-half the field-of-view. It will be understood that the angular deflection of the rays varies continuously from one-quarter the field-of-view to one-half the field-of-view as the lateral displacement is continuously varied from 90 to 180 degrees of phase. It will also be understood that as the lateral displacement is continuously varied from 180 to 360 degrees of phase, the beam deflected by one-half the field-of-view in the direction of displacement of sheet 9 will pass out of the field-of-view and disappear, and that the beam deflected in the opposite direction will vary continuously from a deflection of one-half the field-of-view to zero.

It will be understood that if instead of keeping the radiation beam and first screen fixed, and displacing the second screen, the radiation beam and second screen are fixed and the first screen is displaced, then the collimated beam deflects in a direction opposite to the displacement of the first screen. It will also be understood that the second lenticular sheet 3, 6, or 9 can be displaced laterally by multiples of the width of a lenticule, or displaced along the longitudinal axes of the lenticules without any change in the direction of the collimated beam.

It is important in conducting these measurements that the longitudinal axes of the lenticules in the first and second screens be substantially parallel to each other.

For each additional relative displacement of the screens by one lenticule, or 360 degrees of phase, the beam's deflection proceeds from zero to its maximum angle, at which point it has split into two beams, following which, the newly appeared beam's deflection proceeds from the maximum angle toward zero. By counting the number of times that the deflection of the beam passes through zero in a given direction, one has a measure of the displacement of the screens relative to each other in units of the width of a lenticule. Improved resolution, to a fraction of width of a lenticule, is accomplished by measuring the deflection of the beam as a fraction of the field-of-view. Both the count of zero crossings and measurement of deflection can be accomplished with a detector array whose output is read and processed by a microcontroller, microprocessor or computer. The result can be sent from the microcontroller to a display.

The linear position can be encoded for future reference. The position can be encoded in an electronic memory device such as a computer memory or directed to a display device, recording device, hard copy device, warning device, tool, or print head. The position can be encoded in terms of x and y coordinates of the position. Also, a hard copy of the encoding can be made. Alternatively, the linear position can be physically encoded on the lenticular sheet by marking, which includes making a reference cut. It will be understood that if any object bears a known or calculable position relative to either sheet, then an encoding of its linear position is implied by the encoding of the relative linear position of the screens. The term "encoding" refers to all of these methods of retaining the linear position which have been determined by this invention.

It will be understood that the resolution obtainable by this method of encoding position depends on the number of detector resolution elements within the field-of-view provided that the beam is not greatly oversampled. It will be understood that the resolution will also depend on how many bits are used to encode the output from the detector array.

Many algorithms, such as centroiding, thresholding and averaging, or maximum value can be used by the microcontroller to determine the beam's position. A preferred algorithm for a linear detector with n elements indexed from 0 to n−1 subtending the field-of-view of the lenticular material from left to right and having outputs $D_i$, consists of initially thresholding each element output by setting that output to zero unless $D_i$ is greater than some threshold T. A suitable threshold could be $\frac{1}{5}$ of the expected maximum value. Next, in order to determine whether there are two spots, which occurs near 180 degrees of phase, the quantities $$S_L = \sum_{i=0}^{i=0.25n} D_i \text{ and } S_R = \sum_{i=0.75n}^{n-1} D_i$$

are calculated. If both are zero, the spot is near the center of the array; if both are nonzero, the spot is near 180 degrees of phase; and if only one is nonzero, the spot is near either the left or right ends. A centroid calculation can next be used to obtain the position of the spot. When the spot is near the center, the position in units of detector elements is $$x = \left[\sum_{i=0.25n}^{0.75n} iD_i\right] / \sum_{i=0.25n}^{0.75n} D_i.$$

When the spot is near 180 degrees the larger of $S_L$ and $S_R$ can be used to determine which two quadrants to perform the above centroid calculation in, i.e., i=n/2 to i=n for $S_L<S_R$ and i=0 to i=n/2 for $S_L>S_R$. If $S_L=S_R$ the spot is exactly at 180 degrees. If only one of $S_L$ and $S_R$ are nonzero, the centroid calculation is performed in either the left or right halves of the detector, respectively. The processor continually monitors the value of x and must keep track of how many times the beam has crossed the center of the field-of-view, $x_c$=n/2, in a given direction. If the previous value of x is $x_p$ and the number of times that the beam has crossed $x_c$ from left to right from some starting position is N, then N is incremented by 1 if ($x \geq n/2$ and $x_p<n/2$ and $(x-x_p)<n/2$). Also, N is decremented by 1 if ($x<n/2$ and $x_p>n/2$ and $(x_p-x)<n/2$). Finally, the displacement of the lenticular screens relative to each other and relative to some starting position in units of the width of a lenticule can be expressed as X=N+(x−n/2)/n.

The method described above uses two lenticular screens, with one fixed relative to the radiation source and the other movable. The fixed one can be called the reference screen and need not be much larger than the width of the radiation beam. The length of the movable screen determines the span of length that can be encoded. Screens of more than 40 inches have been encoded. In the configuration of screens shown in FIGS. 1, 2, and 3, both screens present their plane faces P towards the incident radiation beam, but either the convex or plane face of either or both screens can face the incident beam.

Figure 4:
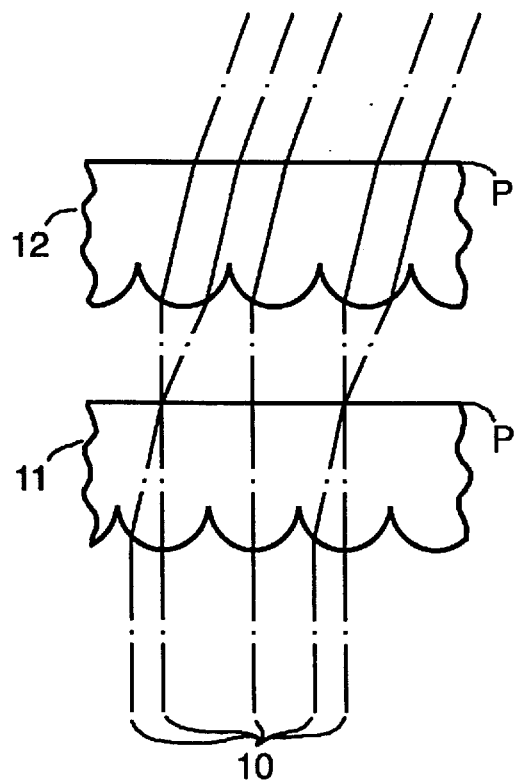
FIG. 4 illustrates the recollimation and deflection of a beam of radiation when the both lenticular sheets presents their convex sides to the incoming radiation and the relative lateral offset between sheets is about one-quarter lenticule or 90 degrees of phase.

FIG. 4 illustrates the deflection and recollimation of the beam when both screens present their convex faces towards the incident beam and the lenticular screens are displaced laterally relative to each other by about one-quarter of the width of a lenticule or 90 degrees of phase. Rays 10, which comprise part of a perpendicularly incident collimated beam of radiation, are focused onto the principal focal plane of lenticular sheet 11, which is approximately coincident with the plane surface P of lenticular sheet 11. Lenticular sheet 12 located with its principal focal plane approximately coincident with the principal focal plane surface of sheet 11, recollimates the rays but deflects them in the direction of its displacement relative to sheet 11 by about one-quarter the field-of-view.

Figure 5:
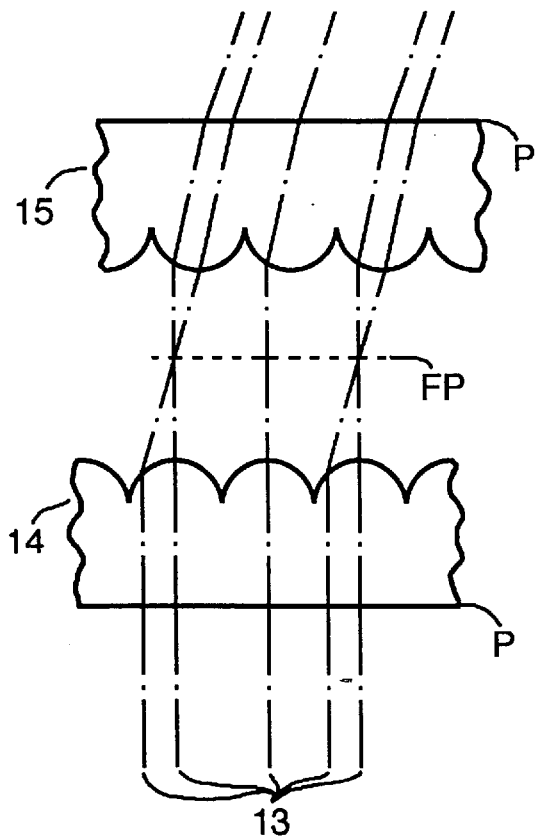
FIG. 5 illustrates the recollimation and deflection of a beam of radiation when the first lenticular sheet presents its plane side and the second lenticular sheet presents its convex side to the incoming radiation and the relative lateral offset between sheets is about one-quarter lenticule or 90 degrees of phase.

FIG. 5 illustrates the deflection and recollimation of the beam when the first screen 14 presents its plane face P and the second screen presents its convex face towards the incident beam and the lenticular screens are displaced laterally relative to each other by about one-quarter of the width of a lenticule or 90 degrees of phase. Rays 13, which comprise part of a perpendicular incident collimated beam of radiation are focused onto the principal focal plane FP of lenticular sheet 14. Lenticular sheet 15 located with its principal focal plane FP approximately coincident with the principal focal plane surface of sheet 14, recollimates the rays but deflects them in the direction of its displacement relative to sheet 14 by about one-quarter the field-of-view.

Figure 6:
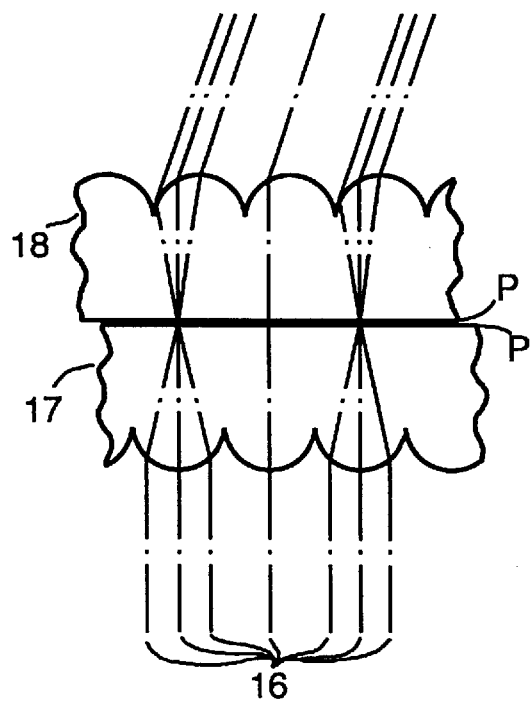
FIG. 6 illustrates the recollimation and deflection of a beam of radiation when the first lenticular sheet presents its convex side and the second lenticular sheet presents its plane side to the incoming radiation and the relative lateral offset between sheets is about one-quarter lenticule or 90 degrees of phase.

FIG. 6 illustrates the deflection and recollimation of the beam when the first screen presents its convex face and the second screen presents its plane face towards the incident beam and the lenticular screens are displaced laterally relative to each other by about one-quarter of the width of a lenticule or 90 degrees of phase. Rays 16, which comprise part of a perpendicular collimated beam of radiation are focused onto the principal focal plane of lenticular sheet 17, which is approximately coincident with the plane surface P of lenticular sheet 17. Lenticular sheet 18 located with its principal focal plane approximately coincident with the principal focal plane and plane surface P of sheet 17, recollimates the rays but deflects them in the direction of its displacement relative to sheet 17 by about one-quarter the field-of-view.

It will be understood that the configuration shown in FIG. 5 permits the widest gap between the lenticular sheets and that the configuration shown in FIG. 6 yields the smallest gap between the lenticular sheets. It will be understood that the construction of a workable encoder based on the configuration of FIG. 6 may require using a lubricating film between the sheets or the manufacture of sheets of slightly thinner dimensions so that the principal focal planes lie outside the material. It will also be understood that some configurations of the lenticular sheets will suffer less from spherical and other types of aberrations, and that the surface curvature can be optimized during manufacture to minimize such aberrations.

Figure 7:
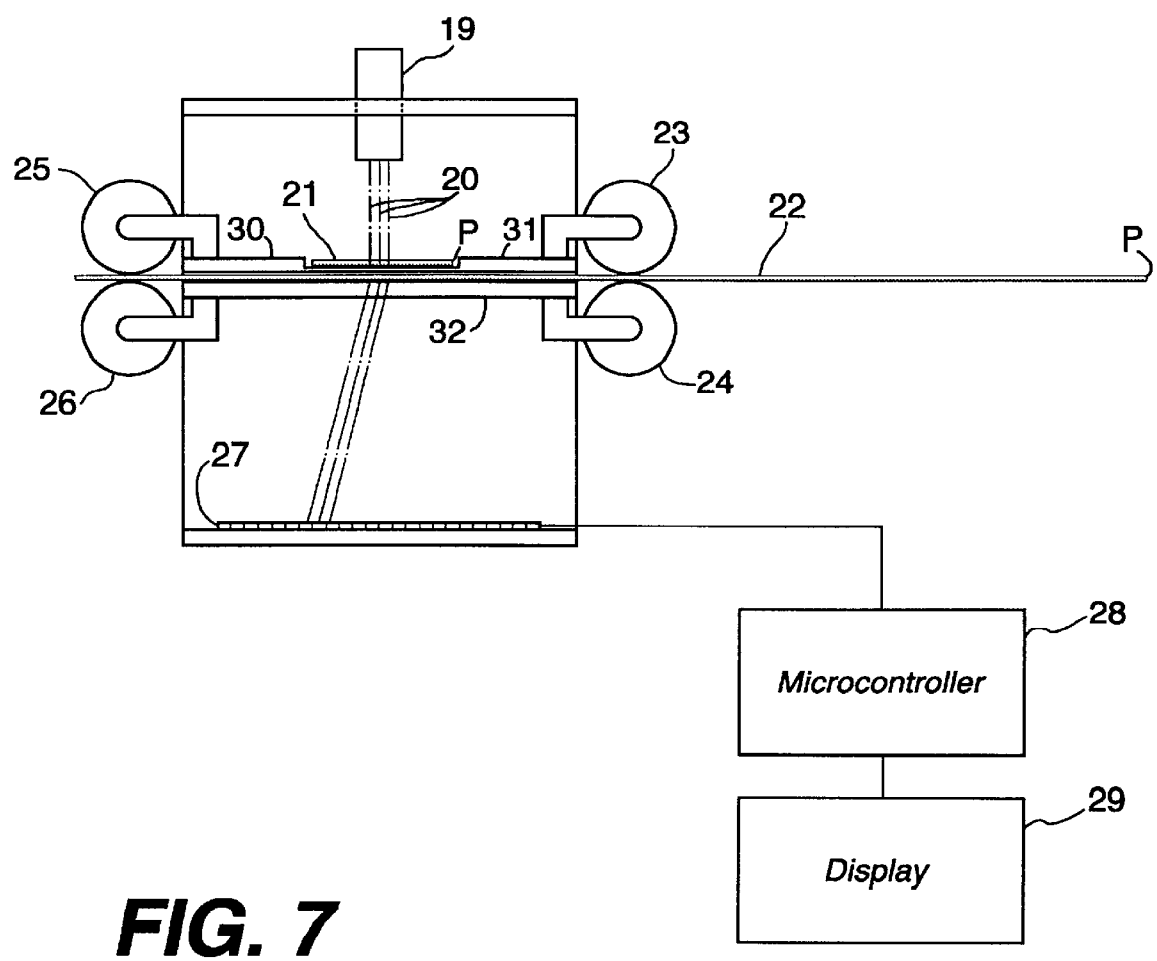
FIG. 7 is a schematic illustration of a linear lenticular encoder in which both lenticular sheets present their plane sides to the incoming radiation and the movable sheet is constrained by rollers.

An embodiment for practicing the method of this invention is shown in FIG. 7. Numeral 19 indicates a source of collimated radiation which can be a laser, which provides a substantially parallel beam of rays 20 to illuminate a plurality of lenticules on lenticular screen 21. Both the planar surface of screen 21 and screen 22 present their plane sides P to the incoming radiation. Screen 21 is the reference screen; the relationships between the reference screen 21 and the lenticular screen 22, which is to be encoded, are illustrated in FIGS. 1, 2 and 3. Screens 21 and 22 are spaced apart in accordance with the principle discussed in connection with the description of FIG. 1. Rays 20 enter the plane surface P of the screen 21, are brought to a focus in the principal focal plane of the screen, and illuminate lenticular screen 22 which is located in a plane substantially parallel to screen 21, oriented with its longitudinal axes substantially parallel to those of screen 21, spaced so that its plane surface P is substantially in the principal focal plane of screen 21, and has a pitch similar to that of screen 21. The rays are recollimated by screen 22 and are detected by detector array 27, which can be a linear or one-dimensional detector. The output from the detector is fed to microcontroller 28 where it is processed to determine the location of the beam within the field-of-view of the lenticules, and to keep count of the number of transits and fractions thereof of the center of the field-of-view by the beam as sheet 22 moves horizontally in the figure. Microcontroller 28 can display the accumulated count of transits and fractions of transits in units of lenticules or other units on the display device 29 or the position can also be encoded in the microcontroller's memory. Lenticular sheet 22 can be held in its proper orientation and spacing relative to sheet 21 and constrained in its direction of travel by guides 23, 24, 25, and 26 which can be rollers. Guides 30 and 31 hold the reference lenticular sheet 21 in proper position to encode sheet 22. Sheet 22 can be encoded with a mark for future reference. Table 32 is attached to the rollers 23, 24, 25 and 26 and can be adjusted up and down in order to place reference lenticular reference sheet 21 in proper position with the lenticular sheet 22.

In another embodiment of the present invention, lenticular screen 21 can present its convex side to illuminating beam 20 and lenticular screen 22 can present its convex side to the beam, as diagrammed in FIG. 4.

In one embodiment of the present invention, lenticular screen 21 can present its plane side P to illuminating beam 20 and lenticular screen 22 can present its convex side to the beam, as diagrammed in FIG. 5.

In another embodiment of the present invention, lenticular screen 21 can present its convex side to illuminating beam 20 and lenticular screen 22 can present its plane side P to the beam, as diagrammed in FIG. 6.

The above embodiments for practicing this invention show the beam of rays, reference screen, and detector array fixed, and the screen to be encoded as movable. Other embodiments, such as keeping the screen to be encoded fixed, and the beam, reference screen, and detector array movable, or keeping the reference screen, screen to be encoded, and detector array fixed, and the beam movable, or keeping the reference screen and screen to be encoded fixed, and the beam and detector array movable, are valid alternatives.

The above embodiments directly lend themselves to applications such as encoding the position of an XY mechanical stage or the setting of a caliper, thus yielding digital versions of traditional measuring devices. A digital micrometer can be designed from these embodiments by attaching a cable wound around the micrometer shaft to the movable lenticular sheet, and providing sufficient tension to avoid backlash.

Figure 8:
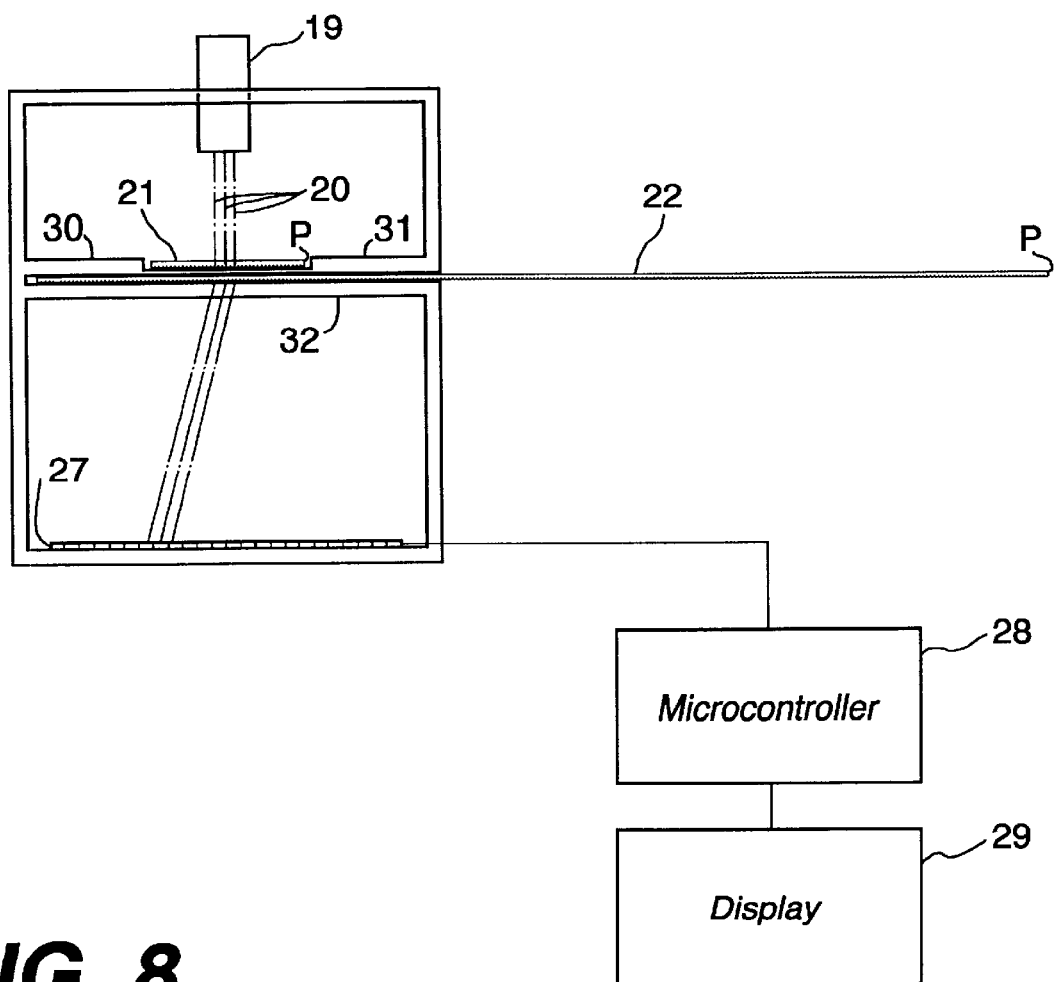
FIG. 8 is a schematic illustration of a linear lenticular encoder in which both lenticular sheets present their plane sides to the incoming radiation and the movable sheet is not constrained as to its direction of travel.

Yet another embodiment of the present invention is shown in FIG. 8. This embodiment is slightly different from that shown in FIG. 7 in that there are no guides to constrain the direction of travel of lenticular sheet 22. The table 32 is held in a fixed position established on the type of method being practiced. However, it should be understood that a mechanism can be provided for adjusting this table 32. This arrangement allows the lenticular sheet to pass through the apparatus in a longitudinal as well as a lateral direction. The positional information in the lateral direction can be used to align a tool or print head or other device to the movable lenticular material, or an object attached to that material, and conversely to align the movable lenticular material or an object attached to that material to a tool or print head or other device.

It is to be understood that the present invention is not limited to the embodiments described above, but encompasses any and all embodiments within the scope of the following claims.

I claim:

1. A method of determining the linear position on a first lenticular screen, by using a reference lenticular screen, said screens being arranged parallel to each other with each screen having a plane surface and a convex surface and a principal focal plane and having a plurality of lenticules of similar pitch with longitudinal axes which are parallel to each other, comprising the steps of:

a) directing a collimated beam of radiation perpendicularly into one lenticular screen;

b) allowing the beam transmitted by said one lenticular screen to enter another lenticular screen, with said lenticular screens being spaced in relationship to each other so as to recollimate the radiation beam upon exit from the other sheet;

c) receiving the recollimated beam exiting from the other lenticular screen on a radiation detector which subtends the field-of-view of the lenticules in the other screen; and d) displacing the lenticular screens relative to each other in a linear direction while sensing the position of the recollimated beam exiting the other screen and calculating the number of lenticules and fractions of lenticules being displaced utilizing the detector array and utilizing means for making such computation.

2. The method of claim 1, wherein said one lenticular screen presents its plane surface towards the incident radiation beam and said other lenticular screen presents it plane surface towards the incident radiation beam and the spacing between the screens is such that the principal focal plane of said one screen substantially coincides with the plane surface of said other screen.

3. The method of claim 1, wherein said one lenticular screen presents its convex surface towards the incident radiation beam and said other lenticular screen presents its convex surface towards the incident radiation beam and the spacing between the screens is such that the principal focal plane of said other screen substantially coincides with the plane surface of said one screen.

4. The method of claim 1, wherein said one lenticular screen presents its plane surface towards the incident radiation beam and said other lenticular screen presents its convex surface towards the incident radiation beam and the spacing between the screens is such that the principal focal plane of said one screen substantially coincides with the principal focal plane of said other screen and is located approximately midway in the spacing between the two screens.

5. The method of claim 1, wherein said one lenticular screen presents its convex surface towards the incident radiation beam and said other lenticular screen presents its plane surface towards the incident radiation beam and the spacing between the screens is such that the principal focal plane of said one screen substantially coincides with the principal focal plane of said other screen and is located approximately in the plane surfaces of both screens.

6. The method of claim 1, wherein the collimated beam of radiation is laser light.

7. The method of claim 1, wherein the radiation detector is a linear array detector.

8. The method of claim 1, wherein the radiation detector is a two-dimensional array detector.

9. The method of claim 1, wherein the beam entering the radiation detector passes through a filter designed to pass substantially all of the wavelengths of the beam and exclude ambient radiation wavelengths.

10. The method of claim 1, wherein the position of the beam exiting the other screen and the number of transits and fractions thereof of the beam across the field-of-view of the lenticules are manually determined.

11. The method of claim 1, in which the determined linear position is encoded using encoding means.

12. The method of claim 11, in which the encoding means is an electronic memory device.

13. The method of claim 11, in which the encoding means is a device making a reference mark on the lenticular screen.

14. The method of claim 1, wherein the position of the beam exiting the other screen and the number of transits and fractions thereof of the beam across the field of view of the lenticules is determined by a microcontroller performing the following steps:

a) determining the beam's position by initially thresholding each element output $D_i$ of the detector array unless $D_i$ is determined to be greater than some threshold value T which may be set at ⅕ of the expected maximum value of $D_i$ with the detector array having n elements indexed from 0 to n−1 subtending the field of view of the lenticular material from left to right; and b) determining whether there are two possible spots at which the beam could be located, which will occur when the first lenticular screen is near 180° of phase, by computing the quantities $$S_L = \sum_{i=0}^{i=0.25n} D_i \text{ and } S_R = \sum_{i=0.75n}^{n-1} D_i,$$

and concluding that if both are zero the spot is near the center of the array, that if both are nonzero the spot is near 180° of phase, and that if only one is nonzero, the spot is near either the left or right ends, where the n detector elements have indexes, i, running from 0 to n−1;

c) using a centroid calculation of $$x = \left[\sum_{i=s}^{f} iD_i\right] / \sum_{i=s}^{f} D_i,$$

to determine the location of the beam in units of detector elements, where i is the detector element index, and s and f are the start and finish indexes, respectively, and the range is substantially the left half, central half, or right half of the detector for a beam spot in the left, central, or right regions of the detector, respectively, and calculated such that when the beam is near 180° of phase the larger of $S_L$ and $S_R$ can be used to determine which two quadrants to perform the above centroid calculation in, i.e., i=n/2 to i=n for $S_L<S_R$, and i=0 to i=n/2 for $S_L>S_R$, but if $S_L=S_R$ the spot is exactly at 180°, and if only one of $S_L$ and $S_R$ are non-zero, the centroid calculation is performed in either the left or right halves of the array detector, respectively, and in making these computations the controller continually monitors the value of x and keeps track of how many times the beam has crossed the center of the field-of-view, $x_c=n/2$, in a given direction, but if the previous value of x is $x_p$ and the number of times that the beam has crossed $x_c$ from left to right from some starting position is N, then N is incremented by 1 if ($x \leq n/2$ and $x_p<n/2$ and $(x-x_p)<n/2$), N is decremented by 1 if ($x<n/2$ and $x_p \leq n/2$ and $(x_p-x)<n/2$) and the displacement of the two lenticular screens relative to each other and relative to some starting position in units of the width of a lenticule can be expressed as X=N+(x−n/2)/n.

15. The method of claim 14, wherein the determined linear position is encoded in an electronic memory device.

16. The method of claim 14, wherein the determined linear position is encoded on the lenticular screen by marking means.

17. An apparatus for determining the linear position on a first lenticular screen, comprising:

a) means for producing collimated radiation;

b) a reference lenticular screen with a plurality of lenticules which can be illuminated by the radiation and held in a position oriented substantially perpendicular to the radiation;

c) said lenticular screens having a similar pitch, oriented substantially parallel to each other, and with the axes of the lenticules of said screens being substantially parallel to each other, and spaced so as to recollimate the radiation beam upon exit from the last screen it exits;

d) means for displacing said screens in relation to each other in a linear direction;

e) means for detecting the recollimated beam within the field-of-view of the lenticules;

f) means for determining the position of the recollimated beam within the field-of-view of the lenticules, and keeping account of the number of transits and fractions thereof of the beam across the field-of-view of the lenticules, due to the linear displacement of the lenticular screens relative to each other.

18. The apparatus of claim 17, wherein the means for producing the collimated radiation is a laser.

19. The apparatus of claim 17, wherein the means for detecting the collimated beam is a linear array detector.

20. The apparatus of claim 17, wherein the means for detecting the collimated beam is a two-dimensional array detector.

21. The apparatus of claim 17, which further includes a filter which is designed to pass substantially all of the wavelengths of the beam exiting the last screen and exclude ambient radiation wavelengths before being detected by the detecting means.

22. The apparatus of claim 17, wherein the means for determining the position of the beam exiting the last screen and the means of keeping account of the number of transits and fractions thereof of the beam across the field-of-view of the lenticules is accomplished manually.

23. The apparatus of claim 17, wherein the apparatus has means for outputting the linear displacement of the first screen relative to the reference screen and has means for encoding this linear displacement.

24. The apparatus of claim 23, in which the means for encoding the linear displacement is an electronic memory device.

25. The apparatus of claim 23, in which the means for encoding the linear displacement is a marking device for marking a reference point on the first screen.

26. The apparatus of claim 17, wherein the means for determining the position of the recollimated beam within the field-of-view of the lenticules and keeping a count of the number of transits and fractions thereof of the beam across the field-of-view of the lenticules is a microcontroller programmed to perform the following steps:

a) determining the beam's position by initially thresholding each element output $D_i$ of the detector array unless $D_i$ is determined to be greater than some threshold value T which may be set at ⅕ of the expected maximum value of $D_i$ with the detector array having n elements indexed from 0 to n−1 subtending the field of view of the lenticular material from left to right; and b) determining whether there are two possible spots at which the beam could be located, which will occur when the first lenticular screen is near 180° of phase, by computing the quantities $$S_L = \sum_{i=0}^{i=0.25n} D_i \text{ and } S_R = \sum_{i=0.75n}^{n-1} D_i,$$

and concluding that if both are zero the spot is near the center of the array, that if both are nonzero the spot is near 180° of phase, and that if only one is nonzero, the spot is near either the left or right ends, where the n detector elements have indexes, i, running from 0 to n−1;

c) using a centroid calculation of $$x = \left[\sum_{i=s}^{f} iD_i\right] / \sum_{i=s}^{f} D_i,$$

to determine the location of the beam in units of detector elements, where i is the detector element index, and s and f are the start and finish indexes, respectively, and the range is substantially the left half, central half, or right half of the detector for a beam spot in the left, central, or right regions of the detector, respectively, and calculated such that when the beam is near 180° of phase the larger of $S_L$ and $S_R$ can be used to determine which two quadrants to perform the above centroid calculation in, i.e., i=n/2 to i=n for $S_L<S_R$, and i=0 to i=n/2 for $S_L>S_R$, but if $S_L=S_R$ the spot is exactly at 180°, and if only one of $S_L$ and $S_R$ are non-zero, the centroid calculation is performed in either the left or right halves of the array detector, respectively, and in making these computations the controller continually monitors the value of x and keeps track of how many times the beam has crossed the center of the field-of-view, $x_c=n/2$, in a given direction, but if the previous value of x is $x_p$ and the number of times that the beam has crossed $x_c$ from left to right from some starting position is N, then N is incremented by 1 if ($x \leq n/2$ and $x_p<n/2$ and $(x-x_p)<n/2$), N is decremented by 1 if ($x<n/2$ and $x_p \leq n/2$ and $(x_p-x)<n/2$) and the displacement of the two lenticular screens relative to each other and relative to some starting position in units of the width of a lenticule can be expressed as X=N+(x−n/2)/n.

27. The apparatus of claim 26, wherein the apparatus has means for outputting the linear displacement of the first screen relative to the reference screen and has means for encoding the linear displacement.

28. The apparatus of claim 27, in which the means for encoding the linear displacement is an electronic memory device.

29. The apparatus of claim 27, in which the means for encoding the linear displacement is a marking device for marking a reference point on the first screen.

* * * * *